United States Patent [19]

Fuerthbauer et al.

[11] Patent Number: 4,863,244
[45] Date of Patent: Sep. 5, 1989

[54] ELECTRO-OPTIC WELDING LENS ASSEMBLY

[75] Inventors: Rupert Fuerthbauer, Lichtensteig; Daniel Stanelli, Ebnat Kappel, both of Switzerland

[73] Assignee: Optrel AG, Ebnaterstrasse, Switzerland

[21] Appl. No.: 183,915

[22] Filed: Apr. 20, 1988

[30] Foreign Application Priority Data

Mar. 11, 1988 [EP] European Pat. Off. ........... 88810154

[51] Int. Cl.$^4$ .................. G02F 1/133; G09G 3/36; A61F 9/00; A61F 9/02
[52] U.S. Cl. .................................. 350/332; 340/784; 2/8; 2/431
[58] Field of Search .................. 350/332; 340/784; 2/431, 426, 15, 410, 8

[56] References Cited

U.S. PATENT DOCUMENTS

| | | | |
|---|---|---|---|
| 3,873,804 | 3/1975 | Gordon | 350/331 R |
| 4,039,803 | 8/1977 | Harsch | 350/332 |
| 4,279,474 | 7/1981 | Belgorod | 350/331 R |
| 4,620,322 | 11/1986 | Eggenschwiler et al. | 350/331 R |

Primary Examiner—John S. Heyman
Assistant Examiner—Anita E. Pellman
Attorney, Agent, or Firm—Tarolli, Sundheim & Covell

[57] ABSTRACT

An electro-optic welding lens assembly for use in a welder's helmet or a protective eyeshield and including at least one liquid crystal filter element adapted to be controlled with regard to its light transmission as well as control means for changing the rate of light transmission of the liquid crystal filter element. The control means comprises a first manually adjustable control circuit operating independently of the amount of light falling on the lens assembly and including means for adjusting the rate of light passing through the liquid crystal filter element. Further, there is provided a second automatically operated control circuit operating in relation to the amount of light falling on the lens assembly. The second control circuit operates only within a range of light intensity above a predetermined threshold value to limit the rate of transmission of light passing through the liquid crystal filter element. The second control circuit overrides and compensates, respectively, the effect of the first control circuit in the range above the threshold value of light intensity falling on the lens assembly with the effect that the lens assembly cannot be opened too much if harmful light rays are present in the ambient environment.

10 Claims, 2 Drawing Sheets

ELECTRO-OPTIC WELDING LENS ASSEMBLY

FIELD OF THE INVENTION

The present invention relates to an electro-optic welding lens assembly which is, for instance, useful in a welder's helmet in a protective eyeshield to protect the eyes of a welder against the glare of a welding arc or welding flame.

BACKGROUND OF THE INVENTION

It is well known that an extremely bright light which may contain a considerable amount of ultraviolet as well as infrared rays is produced by a welding operation. Extended exposure to such bright light rays may be very harmful to the welder's eye. Thus, it is a common practice that welders make use of a helmet with a protective light filter arranged in front of his eyes, or of a protective shield comprising a protective filter and manually held in place between the welder's eyes and a welding arc or flame.

A basic problem with such protective equipment is that the visible light is also greatly attenuated, making it difficult for the welder to clearly see the area of work at the beginning of the welding operation or after having finished it.

Prior Art

In U.S. Pat. No. 3,873,804, a welder's helmet is disclosed using a liquid crystal shutter element to protect the welder's eyes from harmful light rays. Thereby, it is possible to control the rate of light transmission through the filter assembly by applying an electric voltage to the liquid crystal material of the shutter element. A further improved protection may be achieved by a lens assembly as disclosed in U.S. Pat. No. 4,039,254. Due to the fact that two liquid crystal light shutters and three polarizers are used alternately in tandem, a minimum light transmission rate of about 0.01% may be achieved during the time the lens assembly is fully activated.

In German Patent Publication DE-OS 24 42 998, a welding lens assembly is disclosed comprising an automatic control of the light transmission rate. Primarily, it is also intended for use in a protective device for welders and includes, as a protective light shutter element, a liquid crystal element as well. The amount of light arriving at the back side of the shutter element, i.e., the light passing through the shutter element, is monitored by a photo-electric sensing means which is connected to a control circuit. The signal provided by the sensing means serves as a servo signal influencing the control circuit. Thereby, the voltage applied to the liquid crystal element is changed such that the amount of the light passing through the liquid crystal element is fixed to an essentially constant level. A photo-electric transducer is provided at the edge of the shutter element and serves to supply electric power to the liquid crystal shutter element and to the electronic control circuit.

However, practice has shown that light protection devices having an automatic control of the rate of light transmission have proven impractical in welding operations since they are factory adjusted to a predetermined value of transmission of light which cannot be changed by the operator. Particularly, great variations regarding the illuminance of the ambient field may impair the proper function of the control circuit. This is the reason why manually adjustable light protective devices are preferred in the field of welding. Such devices enable the operator to adjust the rate of light transmission individually, depending on the welding process, on the illuminance of the ambient area and on the individual sensitivity of the operator's eyes; thus, the welding operation can be perfectly observed. Furthermore, practice has shown that the sensitivity of a human eye is decreased with increasing age; for instance, a welding operator having an age of, e.g., 45 years needs as much as five times the light intensity to properly observe the operating field as a person having an age of 20 years.

However, if an electro-optic welding lens assembly providing the possibility of manually adjusting the rate of light transmission is used, there is a danger that the assembly might be improperly adjusted or the setting of the adjusting means could be botched inadvertently; under certain circumstances, this misadjustment would lead to an extensive transmission of light rays to the operator's eyes which can be very disturbing or even harmful to health. Such an improper adjustment is possible, for instance, due to external influences, e.g., if an obstacle touches the adjusting means of the device, or if the operator is subjected to a sudden change of light intensity without having readjusted his protective device.

OBJECTS OF THE INVENTION

The object of the present invention, therefore, is to provide an electro-optic welding lens assembly for use in a welder's helmet or a protective eyeshield, and which includes a liquid crystal filter element adapted to be controlled with regard to its light transmission and avoids the disadvantages of the above-mentioned automatic as well as of the manually adjustable protective devices.

A further object of the invention is to provide an assembly of the kind mentioned above that allows an adaption of light transmission characteristics to the individual requirements within a broad range that allows to use one single electro-optic shutter element only for the entire range of protection and of welding technologies.

A still further object of the invention is to provide means operationally connected to a welding lens assembly of the kind mentioned above and which renders impossible an inadvertent misadjustment of the control means serving to regulate the rate of light passing through the liquid crystal filter element and thereby allows to avoid an extensive transmission of light rays through the lens assembly.

SUMMARY OF THE INVENTION

In order to meet these and other objects, the invention provides an electro-optic welding lens assembly for use in a welder's helmet or a protective eyeshield and including a liquid crystal filter element adapted to be controlled with regard to its light transmission as well as control means for changing the rate of light transmission of the liquid crystal filter element. The control means is operatively connected to the liquid crystal filter element and comprises a first manually adjustable control circuit operating independently of the amount of light falling on said lens assembly. The manually adjustable control circuit includes means for adjusting the rate of light passing through the liquid crystal filter element.

Further, there is provided a second automatically operated control circuit operating in relation to the amount of light falling on the lens assembly.

Generally, the second control circuit operates only with a range of light intensity above a predetermined threshold value to limit the rate of transmission of light passing through the liquid crystal filter element. In order to provide the desired protection against inadvertent misadjustment of the device, the second control circuit overrides and compensates, respectively, the effect of the first control circuit in the range above the threshold value of light intensity falling on the lens assembly.

Depending on the individual application of the electro-optic welding lens assembly, two modes of design and, consequenctly, two modes of operation are possible:

In a first mode of operation, the effect of the first control circuit in the range above the threshold value of light intensity falling on the lens assembly is such that the rate of transmission of the liquid crystal filter element cannot be increased by means of the first manually adjustable control circuit if the amount of light falling on the lens assembly is above the threshold value.

In a second mode of operation, the effect of the first control circuit in the range above the threshold value of light intensity falling on the lens assembly is such that the rate of transmission of the liquid crystal filter element is automatically decreased by means of the second control circuit if the amount of light falling on the lens assembly is above the threshold value.

In a region below the above-mentioned threshold value of light intensity, the lens assembly of the invention is manually adjustable such that the rate of light transmission may be changed between a minimum value and a maximum value, independently of the intensity of the light falling on the lens assembly.

Usually, the control means includes a power supply means incorporating at least one source of voltage and connected to the liquid crystal filter element, the liquid crystal filter element having a characteristic such that its rate of light transmission decreases when the voltage applied thereto increases and that its light transmission increases when the voltage applied thereto decreases. Thus, the range of adjustment of the manually operated control circuit corresponds to a certain voltage range whereby the transmission of the light through the liquid crystal filter element is maximal if the control voltage applied to the filter element is approximately zero. By shifting this voltage range to a higher potential, it is possible to realize that the range of adjustment ends at a certain lower value of voltage which is more than zero; consequently, the rate of transmission of the liquid crystal filter element cannot be adjusted to its maximal value anymore.

In accordance with a preferred embodiment of the invention, the power supply means of the assembly includes a source of voltage to control the transmission of the liquid crystal filter element, the value of the voltage provided by the source of voltage increasing essentially proportionally with the intensity of light falling on the lens assembly, starting at a certain threshold value. This increase of the voltage depending on the intensity of the received light automatically controls the liquid crystal filter element such that its rate of transmission decreases; thus, an inadvertent manual adjustment of the filter element to a value which could be too high is avoided.

The influence of the automatically operating control circuit can be easily adjusted such that the intensity of light received, e.g., by the eyes of a welder, does not exceed a certain harmful value. Due to the fact that the control voltage is available from the above-mentioned power supply, the advantage results that the need to provide an additional photosensor usually required in automatic control circuits, is removed.

Some welding lens assemblies known in the prior art and which may be controlled with regard to their rate of light transmission make use of a solar cell assembly as a power supply unit. Other such known welding lens assemblies incorporate a voltaic cell to supply power to the liquid crystal filter element and to the control circuit. Preferably, the power supply means of the welding lens assembly according to the invention contains both voltage sources of the above-mentioned kind, i.e., a first source of voltage providing a constant output voltage as well as a second source of voltage providing a variable output voltage which depends on the intensity of the received light. In contrast to the welding lens assemblies known in the art, the two sources of voltage are coupled in such way that the welding lens assembly is provided with power only from the second source of power as soon as the output voltage thereof is higher than the constant output voltage of the first source of voltage. With other words, this means that the control voltage for controlling the rate of light transmission of the opto-electric filter element is derived from the first source of voltage having a constant output voltage up to a threshold value depending on the incoming light. As soon as said threshold value is exceeded, the control voltage is increased independently of the intensity of the light. Preferably, the welding lens assembly of the invention comprises, for this purpose, one voltaic cell and one photo-electric transducer, or an array of a plurality of voltaic cells connected in series and a plurality of photo-electric transducers connected in series, the voltaic cell, the photo-electric transducer, and the array of voltaic cells and of photo-electric transducers, respectively, being connected in parallel to each other. Thereby, means are provided to decouple the voltaic cell or cells from the photo-electric transducer or transducers.

In accordance with a further preferred embodiment of the welding lens assembly of the present invention, there is further provided electronic switching means including at least one sensor means exposed to the light falling on the lens assembly. The switching means activates the control means for changing the rate of light transmission of the liquid crystal filter element if the sensor means receives light rays with a varying intensity, i.e., enabling the control means to close the liquid crystal filter element under the influence of the first and second control circuit, and disactivating the control means for changing the rate of light transmission of the liquid crystal filter element if the sensor means receives light rays with a continuous intensity, i.e., keeping the liquid crystal filter element in its fully opened condition.

Considering all the provisions discussed hereinabove, it is clear to every person skilled in the art that the opto-electric welding lens assembly can be realized using standard components whereby the voltaic cell or cells sometimes used as emergency power supply in assemblies known in the art fulfills an important additional function. In the solution according to the invention, the original function, i.e., to provide sufficient power at low ambient light levels, is maintained. Furthermore, it is possible without difficulties to rigidly mount the voltaic cell in the opto-electric welding lens assembly of the invention, i.e., it is not necessary to provide a user-replaceable arrangement of the cell, since the power consumption of the assembly according to the invention is very low.

BRIEF DESCRIPTION OF THE DRAWINGS

The above and other objects and features of the present invention will become even more apparent from the following detailed description of a preferred embodiment, taken in connection with the accompanying drawings, in which.

DETAILED DESCRIPTION OF A PREFERRED EMBODIMENT

Figure 1:
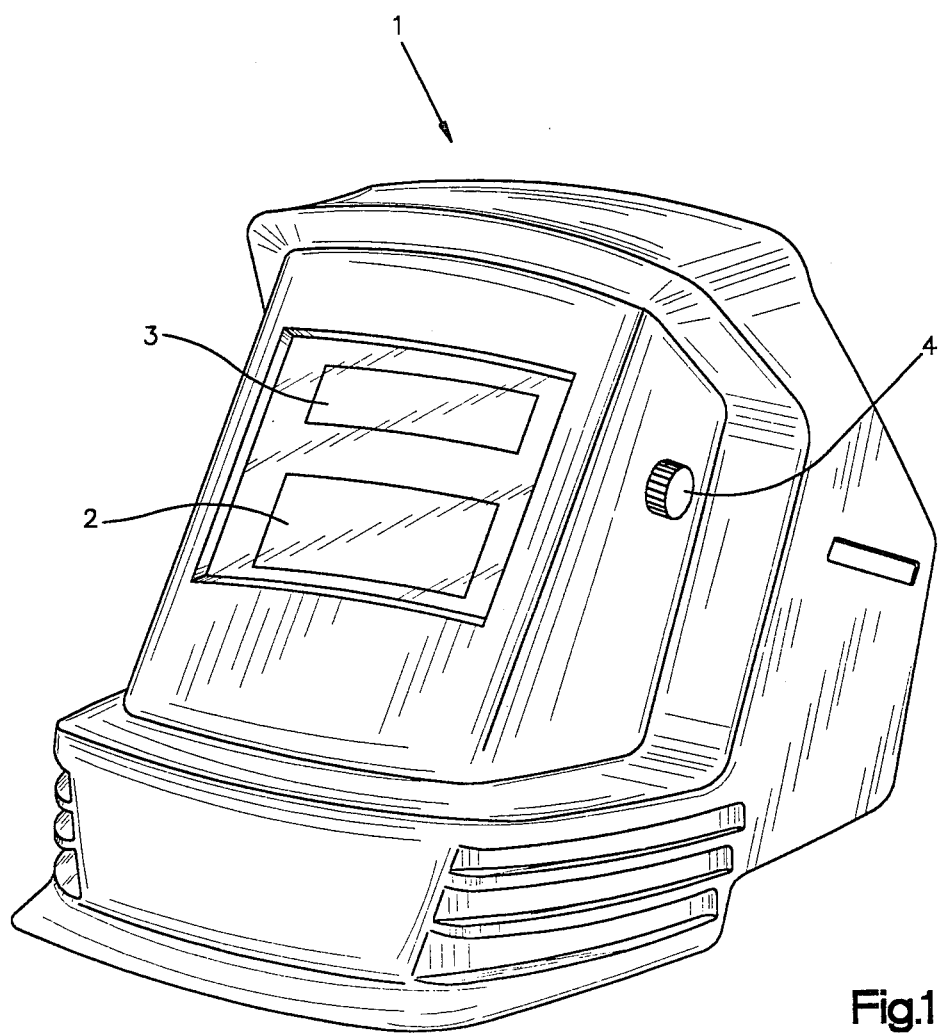
FIG. 1 is a general perspective view of a welder's helmet incorporating the electro-optic welding lens assembly of the invention.

According to FIG. 1, there is shown a welder's helmet, generally designated with reference numeral 1, incorporating the electro-optic welding lens assembly of the invention. It is understood that the shape of the helmet 1 is suitably designed to fit the head of a welder and may comprise (not shown) fixing means to fix the helmet 1 to the welder's head.

On the front side of the helmet 1, there is provided an electro-optic welding lens assembly 2 in a suitable position in front of the eyes of the welder. The design of the electro-optic welding lens assembly is known in the art and it may comprise one or two liquid crystal filter elements which is and are, respectively, in an essentially transparent condition if no power is applied to it or them, respectively, and which is and are, respectively, in a darkened condition if a certain control voltage is applied thereto. The design of such liquid crystal shutter need not be discussed in detail since it is well known in the prior art.

The welder's helmet 1 further includes a solar cell array 3 arranged above the welding lens assembly 2 and forming a part of the control and power supply circuit which will be further discussed hereinbelow.

Furthermore, the helmet 1 incorporates a manually adjustable control member, represented as an adjustment knob 4 which, when rotated, influences the position of a (not shown) potentiometer and forms a part of the previously mentioned control and power supply circuit.

The exact function of the electro-optic welding lens assembly incorporated in the helmet 1 will be discussed later. However, it should be pointed out that the adjustment knob 4 is part of the manual control circuit for the liquid crystal filter element; if the light intensity passing through the liquid crystal filter element is below a certain threshold value, the rate of light transmission passing through the liquid crystal filter element may be adjusted by rotating the adjustment knob 4. Usually, this will be the normal operating range; thus, the welder using the helmet 1 incorporating the welding lens assembly of the invention may adjust the amount of light passing through the liquid crystal filter element according to the individual sensitivity of his eyes.

Figure 2:
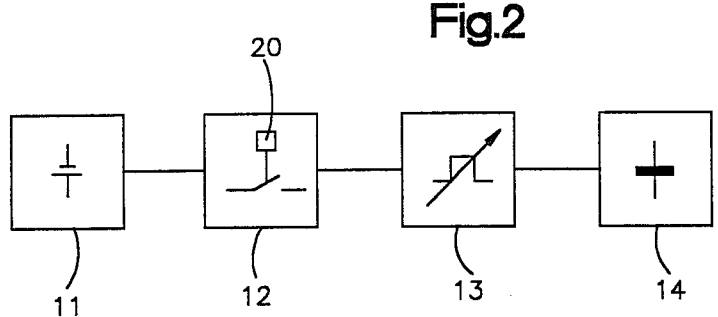
FIG. 2 is a simplified block diagram of the control circuit of the electro-optic welding lens assembly.

As can be seen from the block diagram of FIG. 2, the electro-optic welding lens assembly incorporated in the helmet 1 includes a power supply unit 11, a switching unit 12 controlled by a sensor 20 responsive to the light produced by a welding operation, and a control unit 13 which may be realized in the form of a controllable square wave generator, the pulse width and/or amplitude thereof being manually controllable, e.g., by means of the adjustment knob 4 which influences the resistance value of a potentiometer coupled therewith. All these units 11, 12 and 13 serve to control and operate an electro-optic filter element 14, e.g., a liquid crystal filter element.

The switching unit 12 includes at least one sensor 20 as shown in the block diagram of FIG. 2, prefereably two or even more sensors 20, exposed to the light falling on the lens assembly. As soon as the at least one sensor 20 recognizes that a bright light source is present which emits a not continuous, but a flickering light or a light with a periodically alternating intensity, the switching unit 12 is activated to trigger the control unit 13 with the consequence that the liquid crystal filter element 14 is darkened up to a certain degree which can be adjusted manually. If the flickering or alternating light source disappears, the switching unit 12 returns to its standby condition, thus opening the liquid crystal filter element 14 to its maximal transmission rate.

Figure 4:
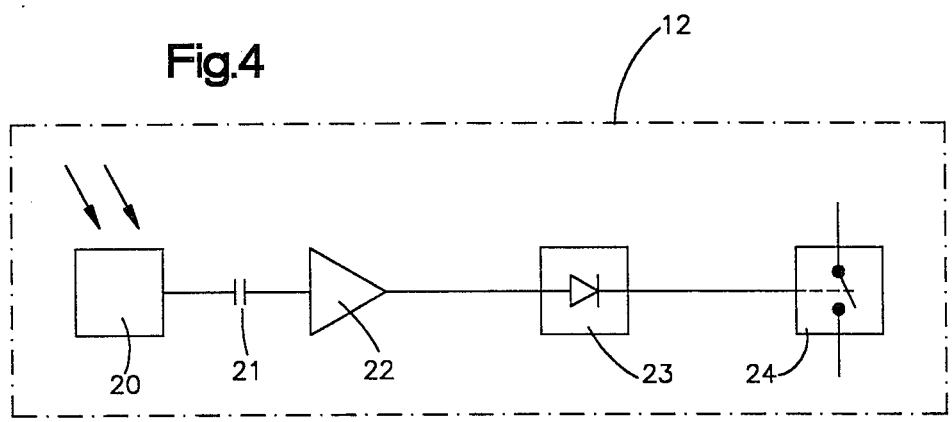
FIG. 4 is a block diagram of the switching circuit.

As can be seen in FIG. 4, the sensor 20 or the plurality of parallel connected sensors 20 is and are, respectively, connected via a capacitor 21 to the input of an AC amplifier 22. If the sensor 20 provides a continuous signal, i.e., a DC voltage, the amplifier 22 delivers no output signal because the DC signal is blocked by the capacitor 21. However, if the signal provided by the sensor 20 contains an alternating component, e.g., when the sensor 20 is exposed to the flickering light of a welding arc, the AC component provided by the sensor 20 is amplified by the amplifier 22 and appears at its output which is connected to the input of a rectifier circuitry 23.

The AC signal delivered by the output of the amplifier 22 is rectified in the rectifier circuitry 23 with the result that a DC signal appears at the output of the recitfier circuitry and is fed to the control input of a semiconductor switch 24, e.g., a field effect transistor. Hence, if a flickering light is recognized by the sensor 20, the switch 24 closes and activates the control circuit of the welding lens assembly. On the other hand, if the sensor 20 receives but a continuous light ray, there is no AC signal to be amplified by the amplifier 22 consequently, the semiconductor switch 24 does not receive a control signal at its input and remains in its open condition. The control circuit for the liquid crystal cell is disconnected from the power supply, and the liquid crystal cell remains open.

Figure 3:
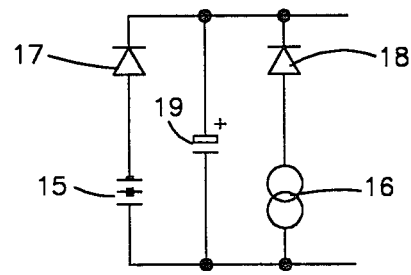
FIG. 3 is a simplified diagram of the power supply unit.

The power supply unit 11 includes, as shown in FIG. 3, a voltaic cell or an array of seriesly connected voltaic cells 15, preferably a lithium battery, as well as a photoelectric transducer 16, for instance, and preferably an array of a plurality of seriesly connected solar cells. The voltaic cell or the array of seriesly connected voltaic cells 15, on one hand, and the photo-electric transducer 16, on the other hand, are connected in parallel. The current loop of the voltaic cell 15 comprises a diode 17, and the current loop of the photo-electric transducer 16 includes a diode 18. Thus, the two voltage sources constituted, on one hand, by the voltaic cell or the array of voltaic cells 15 and, on the other hand, by the array of solar cells 16, are electrically decoupled from each other. Furthermore, a buffer condenser 19 is connected in parallel to the two previously mentioned voltage sources.

It will be readily understood by any person skilled in the art that the voltaic cell provides an essentially constant output voltage during its useful life, independently of the intensity of light falling on the front of the welder's helmet. Contrary to that, the photo-electric transducer 16, e.g., an array of solar cells, will provide an output voltage which largely depends on this light intensity. Since both voltage sources are connected to the control circuit including the switching unit 12 and the control unit 13 adapted to control the rate of light transmission of the liquid crystal filter element, it is clear that the operating conditions of the welding lens assembly will differ independently of the intensity of light falling on the photo-electric transducer 16.

As long as the photo-electric transducer 16 provides an output voltage to the control circuit, the value thereof being below a predetermined threshold value, particularly below the value of the output voltage provided by the voltaic cell 15, the control circuit 12, 13 obtains its power solely from the voltaic cell 15 under this operating condition, the ambient light level is comparatively low; otherwise, the photo-electric transducer would provide a higher output voltage. Thus, it is possible to adjust the rate of light transmission passing through the liquid crystal filter element 14 within a broad range. In other words, the light transmission characteristic of the filter element 14 may be adjusted from a condition, in which essentially no light can pass, up to a condition in which a certain predetermined amount can pass. This feature is very convenient for an operator using the helmet 1 under normal operating conditons.

The operating conditions discussed hereinabove and, consequently, the operating range of the manually adjustable control circuit extend up to a top threshold value of the intensity of light which certainly is not harmful to the eyes of the welder.

If the threshold value is exceeded, the variable output voltage provided by the photo-electric transducer 16 becomes higher and exceeds the value of the output voltage of the voltaic cell 15. As soon as this condition is reached, the manually adjustable control circuit is overriden such that the liquid crystal filter element cannot be adjusted to reach its full transmission but will stop in a condition where a certain reduction of light transmission is ensured, thus protecting the eyes of the operator from excessive light intensity. In other words, the higher output voltage of the photo-electric transducer 16 compensates the influence of the manually adjustable control circuit such that the liquid crystal filter element, however, can be set to its condition of minimum transmission, but cannot be set to its condition of the previously mentioned predetermined maximum transmission.

Usually, the constant output voltage of the voltaic cell 15 is approximately sixty percent of the output voltage of the photo-electric transducer 16. The power supplied by the voltaic cell 15 is sufficient to ensure normal operation of the device. The characteristic of the control circuit 12, 13 can be set such that no harmful light rays can reach the eyes of the operator if the voltaic cell 15 has its nominal voltage. If this threshold value is exceeded, the output voltage provided by the photo-electric transducer 16 will be higher than the output voltage provided by the voltaic cell 15 with the consequence that the liquid crystal filter element cannot be opened anymore up to the previously mentioned predetermined transmission value. Thereby, the higher the output voltage of the photo-electric transducer 16 is, the more the adjustment range of the manually adjustable control circuit will be limited. Such limitation, however, will take place only at the upper end of the adjustment range, i.e., with increasing light intensity, the limit up to which the liquid crystal filter element can be opened, is thereby lowered.

What we claim is:

1. An electro-optic welding lens assembly for use in a welder's helmet or a protective eyeshield, including a liquid crystal filter element adapted to be controlled with regard to its light transmission as well as control means for changing the rate of light transmission of said liquid crystal filter element, said control means comprising:

a first manually adjustable control circuit operating independently of the amount of light falling on said lens assembly and including means for adjusting the rate of light passing through said liquid crystal filter element; and a second automatically operated control circuit operating in relation to the amount of light falling on said lens assembly;

said second control circuit operating only within a range of light intensity above a predetermined threshold value to limit the rate of transmission of light passing through said liquid crystal filter element whereby said second control circuit overrides and compensates, respectively, the effect of said first control circuit in said range above said threshold value of light intensity falling on said lens assembly.

2. An electro-optic welding lens assembly according to claim 1, in which the effect of said first control circuit in said range above said threshold value of light intensity falling on said lens assembly is such that the rate of transmission of said liquid crystal filter element cannot be increased by means of said first manually adjustable control circuit if the amount of light falling on said lens assembly is above said threshold value.

3. An electro-optic welding lens assembly according to claim 1, in which the effect of said first control circuit in said range above said threshold value of light intensity falling on said lens assembly is such that the rate of transmission of said liquid crystal filter element is automatically decreased by means of said second control circuit if the amount of light falling on said lens assembly is above said threshold value.

4. An electro-optic welding lens assembly according to claim 1, in which said control means includes a power supply means incorporating at least one source of voltage, connected to said liquid crystal filter element, said liquid crystal filter element having a characteristic such that its rate of light transmission decreases when the voltage applied thereto increases and that its light transmission increases when the voltage applied thereto decreases;

said at least one voltage source of said power supply means providing a voltage controlling the rate of transmission of said liquid crystal filter element, the value thereof increasing with the amount of light falling on said lens assembly as soon as said threshold value of the intensity of light is exceeded.

5. An electro-optic welding lens assembly according to claim 4, in which said power supply means includes a first source of voltage providing an essentially constant voltage and a second source of voltage providing a voltage essentially dependent on the amount of light falling on said lens assembly.

6. An electro-optic welding lens assembly according to claim 5, in which said first and second sources of voltage are coupled to each other such that only said second source of voltage provides a voltage to said liquid crystal filter element as soon as the value of the voltage of said second source of voltage is higher than the value of the voltage of said first source of voltage.

7. An electro-optic welding lens assembly according to claim 6, in which said first source of voltage comprises at least one voltaic cell and in which said second source of voltage comprises at least one photo-electric transducer.

8. An electro-optic welding lens assembly according to claim 7, in which said at least one voltaic cell and said at least one photo-electric transducer are connected parallel to each other, means being provided to decouple said at least one voltaic cell and said at least one photo-electric transducer from each other.

9. An electro-optic welding lens assembly according to claim 1, further comprising an electronic switching means including at least one sensor means exposed to the light falling on said lens assembly, said switching means activating said control means if said sensor means receives light rays with a varying intensity and disactivating said control means if said sensor means receives light rays with a continuous intensity.

10. An electro-optic welding lens assembly according to claim 9 in which said switching means comprises an AC amplifier, said sensor means being connected to the input thereof, a rectifier circuitry connected to the output of said AC amplifier, and a semiconductor switching means, the control input thereof being connected to the output of said rectifier circuitry.

* * * * *